(12) United States Patent
Józefiak et al.

(10) Patent No.: US 11,470,829 B2
(45) Date of Patent: Oct. 18, 2022

(54) MODULAR LAMP SYSTEM FOR INSECT BREEDING, USE THEREOF FOR STIMULATION OF INSECT REPRODUCTION AND A METHOD OF INSECT BREEDING

(71) Applicant: HiProMine S.A., Robakowo (PL)

(72) Inventors: Damian Józefiak, Poznań (PL); Jan Mazurkiewicz, Sady (PL); Jakub Rudak, Warsaw (PL); Jakub Urbański, Warsaw (PL)

(73) Assignee: HiProMineS.A., Robakowo (PL)

( * ) Notice: Subject to any disclaimer, the term of this patent is extended or adjusted under 35 U.S.C. 154(b) by 260 days.

(21) Appl. No.: 15/748,163

(22) PCT Filed: Jul. 28, 2016

(86) PCT No.: PCT/IB2016/054508
§ 371 (c)(1),
(2) Date: Jan. 26, 2018

(87) PCT Pub. No.: WO2017/017632
PCT Pub. Date: Feb. 2, 2017

(65) Prior Publication Data
US 2018/0220632 A1  Aug. 9, 2018

(30) Foreign Application Priority Data
Jul. 29, 2015 (PL) .......................................... 413265

(51) Int. Cl.
*A01K 67/033* (2006.01)
*A01K 29/00* (2006.01)

(52) U.S. Cl.
CPC ............ *A01K 67/033* (2013.01); *A01K 29/00* (2013.01); *A01K 2227/706* (2013.01)

(58) Field of Classification Search
CPC .................................................... A01K 67/033
(Continued)

(56) References Cited

U.S. PATENT DOCUMENTS 9,510,572 B2 * 12/2016 Aldana ................ A01K 67/033
2008/0134568 A1 * 6/2008 Cowan ..................... A01M 1/04
43/113

(Continued)

FOREIGN PATENT DOCUMENTS

WO  WO 2013/166590  11/2013
WO  WO 2015/023761  2/2015

OTHER PUBLICATIONS

Hori et al., Lethal effects of short-wavelength visible light on insects, Scientific Rep. 4:7383 (2014).
(Continued)

*Primary Examiner* — David J Parsley
(74) *Attorney, Agent, or Firm* — Dilworth IP, LLC

(57) ABSTRACT

The present invention relates to a modular lamp system for insect breeding and reproduction stimulation, which comprises lamps emitting light in the range of about 400-800 nm and at least one lamp with a peak emission lower than about 410 nm, wherein the light intensity measured 50 cm from the light source is not less than 5000 lx with an irradiance in the spectral range of 350-1000 nm at the level of 35-50 W/m2, wherein no less than 95% of the irradiance is in the range of 350-700 nm, and wherein the irradiance in the spectral range of 370-410 nm is 25-80% of irradiance in the range of 350-700 nm and is not less than 10 W/m2. The present invention also provides a method of insect breeding and use of the modular lamp system for stimulation of insect reproduction.

16 Claims, 5 Drawing Sheets

(58) Field of Classification Search
USPC .......................................................... 119/6.5
See application file for complete search history.

(56) References Cited

U.S. PATENT DOCUMENTS

2009/0000553 A1* 1/2009 Ramos Elorduy Y Blasquez .......
A01K 67/033
119/6.5
2014/0020630 A1   1/2014 Courtright

OTHER PUBLICATIONS

Sakai et al., Light wavelength dependency of mating activity in the *Drosophila* melanogaster species subgroup, Genes Genet. Syst. 77:187-195 (2002).

Zhang et al., An artificial lights source influences mating and oviposition of black soldier flies, Hermetia illucens, J. Insect Sci. 10:202 (2010).

Cowan, T., & Gries, G. (2009). "Ultraviolet and violet light: attractive orientation cues for the Indian meal moth, Plodia Interpunctella", Entomologia Experimentalis et Applicata, 131, pp. 148-158.

* cited by examiner

MODULAR LAMP SYSTEM FOR INSECT BREEDING, USE THEREOF FOR STIMULATION OF INSECT REPRODUCTION AND A METHOD OF INSECT BREEDING

CROSS-REFERENCE TO RELATED APPLICATIONS

This application is the National Stage of International Application No. PCT/IB2016/054508, filed on Jul. 28, 2016, and claims the benefit of priority to PL Application No. 413265, filed on Jul. 29, 2015, both of which are hereby incorporated by reference in their entireties for all purposes.

TECHNICAL FIELD

The present invention relates to a modular lamp system for insect breeding, particularly tropical insects. The object of the invention is also a method of insect breeding and the use of modular lamp system to stimulate insect reproduction.

BACKGROUND ART

The use of *hermetia* larvae *Hermetia illucens*, a fly species originating from North America is increasing in the process of utilization and conversion of biomass and organic waste. Due to the specific environmental demands, natural occurrence of the species is limited to a relatively small area in the sub-tropical zone. Specific requirements of the species prevent a yearlong breeding of *hermetia* in the climatic conditions of Central and Northern Europe.

This prevents uncontrolled spread of *hermetia* and its adaptation to the environment as a potentially invasive insect, allowing full control even in cultures on an industrial scale.

At the same time, these requirements impose the use of support systems for the insect reproduction. Similar problem applies to the breeding of other insect species that naturally occur in the Tropics, for example locusts, commonly used in amateur and professional breeding, as food for prosimians, reptiles, amphibians and birds.

From the perspective of *hermetia* reproduction stimulation, key factors mentioned in literature are the intensity of light (Tomberlin J K, Sheppard D C. 2002. Factors Influencing mating and oviposition of black soldier flies (Diptera: Stratiomyidae) in a colony. Journal Entomological Science. 37: 345-352) and light spectral range (Zhang J., Sun M., L. Huang, Z. Liu, He J., Yu Z., Tomberlin J K (2010) An artificial light source influences mating and oviposition of black soldier flies, *Hermetia illucens*. Journal of Insect Science: Vol. 10|Article 202). In industrial conditions, *hermetia* breeding is supported by using iodine-quartz lamps of high power and a very broad spectral range of 350-2500 nm, that goes far beyond the perception of insects—studies by Briscoe et al. (Briscoe A D Chittka L. 2001. The evolution of color vision in insects. Annual Review of Entomology 46: 471-510) indicate, insects perceive visible light in the range up to 700 nm. Said lamps are not dedicated for insect breeding and are not capable of selectively controlling individual spectral ranges.

Due to the emission of radiation in a broad spectral range, lamps are energy-consuming and emit large quantities of thermal radiation. The light of the iodine-quartz lamps is intermittent and importantly for the implementation in *hermetia* reproduction support, the lamp emission spectrum changes over time of use in an uncontrolled manner, while emission in the range of 350-455 nm is significantly reduced.

Alternatively, mesh aviaries in a volume of 2-6 $m^3$ are used with sunlight, this system however excludes a yearlong *hermetia* breeding in temperate climate and prevents precise control of environmental conditions within the aviary (temperature and humidity).

The object of the invention is to provide an efficient system for insect breeding and reproduction stimulation, particularly for stimulation in breeding chambers, especially for insect species which do not originate from the temperate climate. This object has been achieved with the use of the modular lamp system for insect breeding according to the invention, which actively stimulates insects to reproduce and enables efficient breeding particularly for *Hermetia illucens* and locusts, particularly *Locusta migratoria* and/or *Schistocerca gregaria*.

The inventors have found it is feasible to use a lamp system enabling control of irradiance and illumination intensity in individual spectral ranges to stimulate *hermetia* and locusts reproduction, with the assumption that due to the characteristics of insect vision the spectrum will be limited to the wavelength range of 350-800 nm.

Research conducted by the Inventors of the present invention has shown that it is possible to use artificial light to effectively stimulate insect reproduction, including insect species not naturally occurring in temperate climates, in particular the *Hermetia illucens* and locust species, such as *Schistocerca gregaria* and *Locusta migratoria*.

DISCLOSURE OF THE INVENTION

The object of the invention is a modular lamp system for insect breeding and reproduction stimulation which includes lamp emitting light in the range of 400-800 nm and at least one lamp with a peak emission below about 410 nm, wherein the light intensity measured 50 cm from the light source is not less than 5000 lx with irradiance in the spectral range of 350-1000 nm being at the level of 35-50 $W/m^2$, wherein not less than 95% of the irradiance is in the range of 350-700 nm, and wherein the irradiance in the spectral range of 370-410 nm is 25-80% of the irradiance in the range of 350-700 nm and is not less than 10 $W/m^2$. The term "lamp" indicates a single device that may comprise a plurality of light sources emitting light at different wavelengths, especially in the range of 350-1000 nm.

Research conducted by the Inventors confirmed that lighting in the range below about 410 nm, in particular in the range of about 370-410 nm is crucial for the stimulation of insect reproductive behavior, particularly for tropical insects, particularly *hermetia* and locusts. White light in the range of about 400-800 nm have not stimulated insects flight flying and mating activities. As Inventors of present invention surprisingly discovered the addition of the at least one lamp with a peak emission below about 410 nm to the spectral range is sufficient to cause a rapid increase of activity observable after few minutes, and reproductive behavior. The use of the solution according to the invention increases reproduction efficiency by over 50% with respect to the one described in literature.

The essence of the solution according to the invention is the use of lamp module and/or a single lamp comprising a light source giving a sufficiently strong light in the range of 400-800 nm, comprising any lamp known in the art which gives so-called white, cool light, wherein the module further comprises at least one lamp with a peak emission below 410 nm, giving a sufficiently strong light in this range (irradiance in spectral range of 370-410 nm is 25-80% of the irradiance in the range of 350-1000 nm and is not less than 10 W/m$^2$). One skilled in the art will appreciate that there are many possible construction methods of such a module. The module may be constructed in any convenient manner, also with commercially available lamps, preferably LED lamps, depending on the location requirements, the availability of power source, the quantity of insects breeding, etc., and it will fulfill its purpose as long as the lighting parameters are maintained as described above. Lamp parameters specified by the manufacturer were verified by a series of measurements made with the JETI device from Technische Instrumente GmbH.

The solution according to the invention enables easier control of the spectrum emission quality and the replacement of individual lighting modules without replacing the entire lighting installation.

Preferably, all lamps included in the module according to the invention are controlled independently, preferably in a manner allowing to control the intensity of illumination of each lamp in a manner known in the art. Said independent control of each lamp enables easier simulation of the lighting of the natural environment, in terms of both: light intensity and spectral range specific for the latitude of natural occurrence of the bred insect cultures, as well as to easily increase irradiance in the spectral range below about 410 nm, even above the level occurring in the natural environment.

Preferably, the lamps are LED lamps. For example, LED lamps with a nominal power of 20 W can be used. The Inventors have found that the implementation of the system according to the invention allows to reduce energy consumption by about 70% compared to the energy consumption with the use of iodine-quartz lamps with the simultaneous improvement of reproduction efficiency.

Preferably, the intensity of light emitted by the modular system according to the invention in the range of below 410 nm exceeds the intensity of sunlight in this range. As inventors surprisingly found, the total intensity of light and irradiance in the range of the visible spectrum are of secondary importance in insect reproduction stimulation, whereas the solution according to the invention enables achieving increased activity and reproductive behaviors of insects exceeding the values obtained for insects illuminated by sunlight.

In a preferred embodiment, at least one lamp has a peak emission of about 385 nm, that stimulates the insect reproductive behavior.

Preferably, the system according to the invention further comprises a lamp having a peak emission of about 405 nm, that provides additional stimulation for reproductive behavior.

In an embodiment, the system according to the invention comprises lamps of total nominal power of about 120 W.

In a preferred embodiment, the modular lamp system is composed of 6 lamps with a total nominal power of 120 W, including 4 LED lamps emitting "cool white" light in the range of 400-800 nm and 2 lamps with emission peaks respectively of 385 nm and 405 nm. The system provides a highly efficient stimulation of reproductive behavior.

In an embodiment, the system further comprises an additional lamp having a peak emission of about 455 nm, which is advantageous for breeding/rearing locusts.

In an embodiment, the system according to the invention further comprises a lamp having a peak emission of about 375 nm, which provides additional stimulation of reproductive behavior of insects.

Preferably, the system according to the invention is installed in closed breeding chambers, preferably with the height lower than 150 cm, more preferably lower than about 120 cm, more preferably lower than 100 cm, and/or having a bottom surface area in the range of 0.1-1 m$^2$, preferably equal to or less than about 1 m$^2$, 0.8 m$^2$, 0.6 m$^2$, 0.5 m$^2$, 0.4 m$^2$, 0.3 m$^2$, 0.32 m$^2$, 0.2 m$^2$, 0.1 m$^2$.

The object of the invention is also a method of breeding insects and stimulation of reproduction in breeding chambers, wherein the insects are provided with a light source with the use of the modular lamp system according to the invention.

Preferably, the insects are selected from the species native to subtropical and tropical climate zone, non-native to the temperate climate zone, particularly *Hermetia illucens* and locusts, especially *Locusta migratoria* and/or *Schistocerca gregaria*. Insects can be grown for various purposes including the production of food and/or feed, for the recreational, scientific, industrial and other purposes.

In an embodiment, the insects are kept in closed breeding chambers, preferably of a height lower than 150 cm, more preferably lower than about 120 cm, more preferably lower than 100 cm, and/or having a bottom surface area in the range of 0.1-1 m$^2$, preferably equal to or less than about 1 m$^2$, 0.8 m$^2$, 0.6 m$^2$, 0.5 m$^2$, 0.4 m$^2$, 0.3 m$^2$, 0.32 m$^2$, 0.2 m$^2$, 0.1 m$^2$. The solution according to the invention enables significant reduction in the space required for the insect breeding that require proper lighting.

The object of the invention is also a use of a modular lamp system according to the invention for insect reproduction stimulation.

Preferably, the insects are selected from species non-native to the temperate climate zone, in particular *Hermetia illucens* and locusts, especially *Locusta migratoria* and/or *Schistocerca gregaria*.

EXAMPLES

Figure 1:
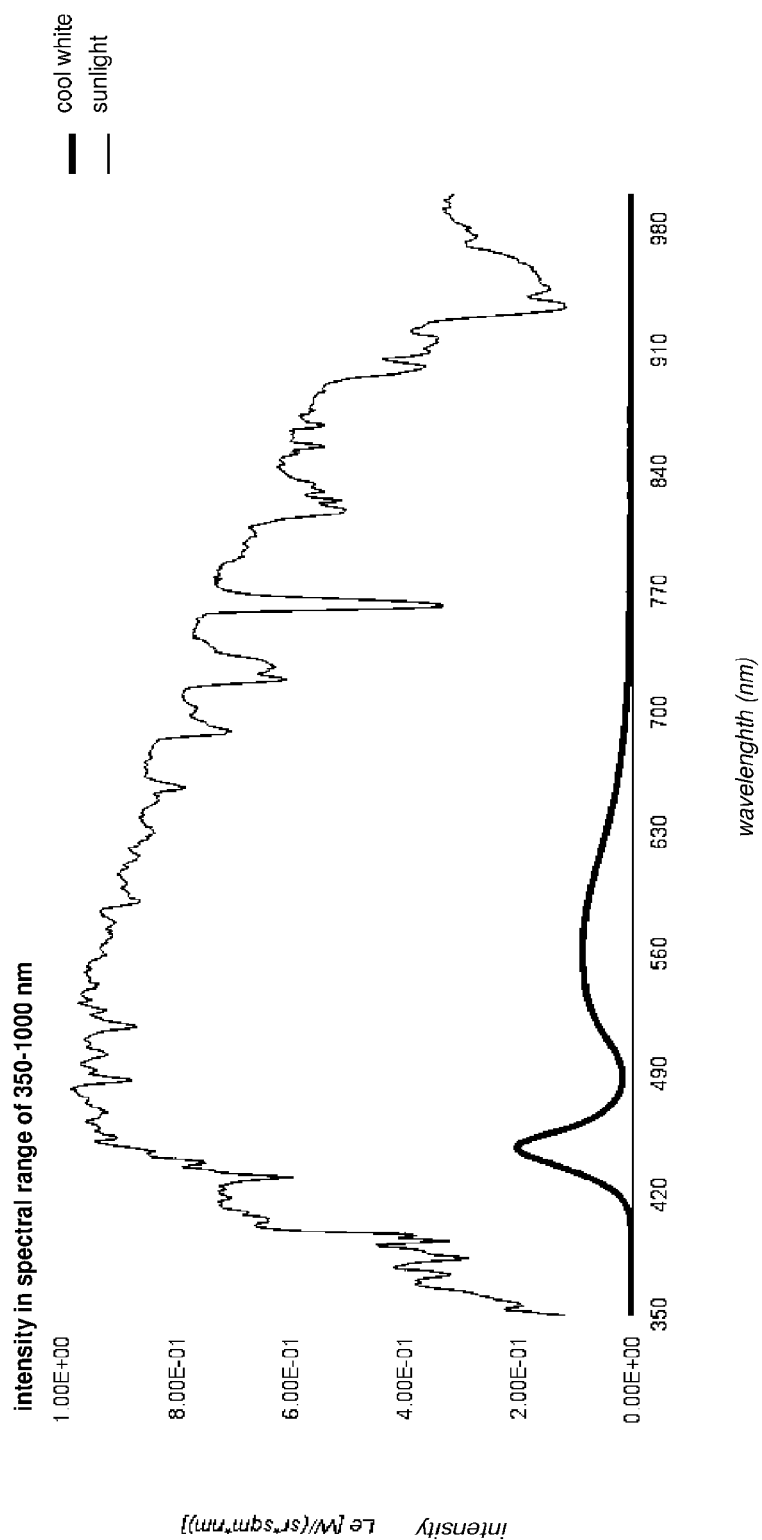
FIG. 1 shows the intensity in spectral range of 350-1000 nm. Combination 1: [cool white], compared with sunlight.
Figure 2:
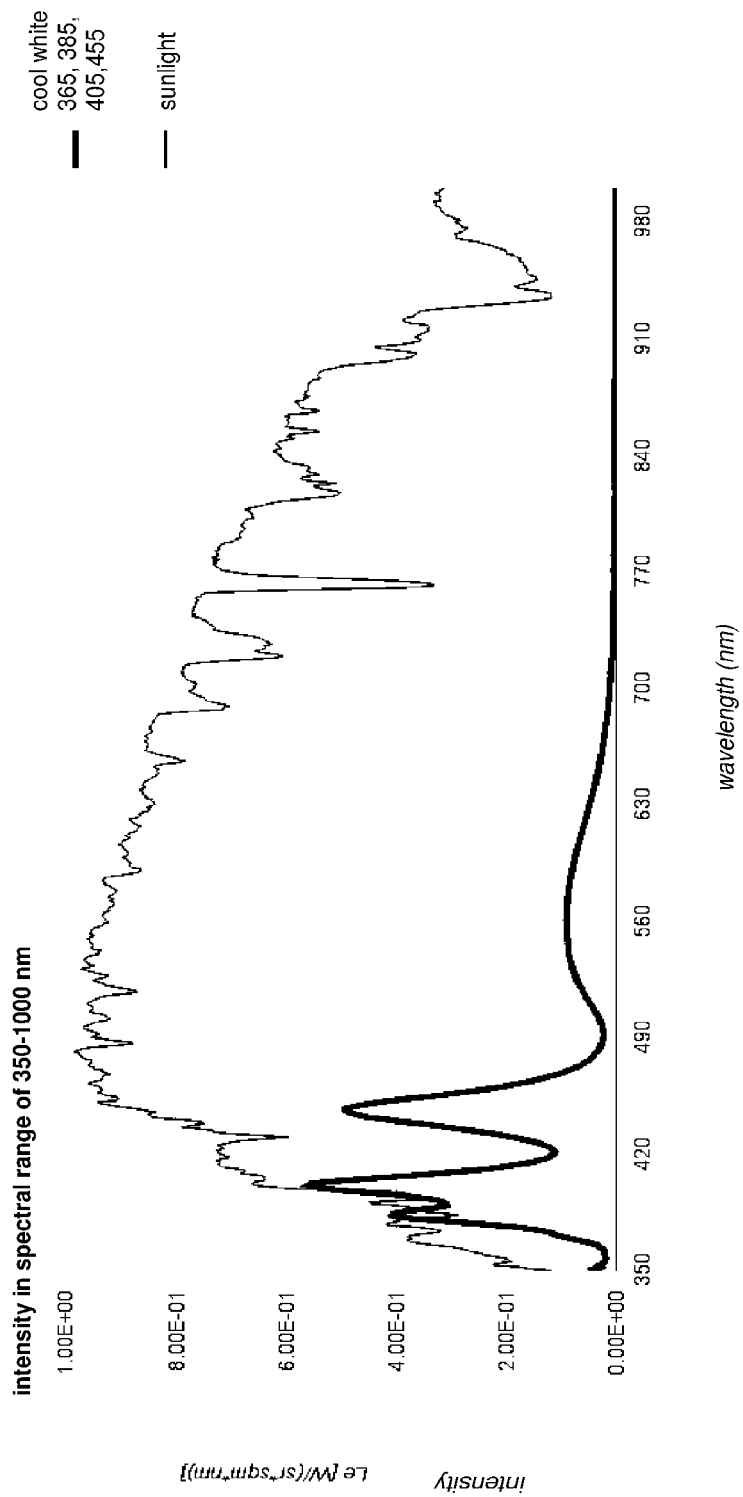
FIG. 2 shows the intensity in spectral range of 350-1000 nm. Combination 2: [cool white, 375 nm, 385 nm, 405 nm, 455 nm], compared with sunlight.
Figure 3:
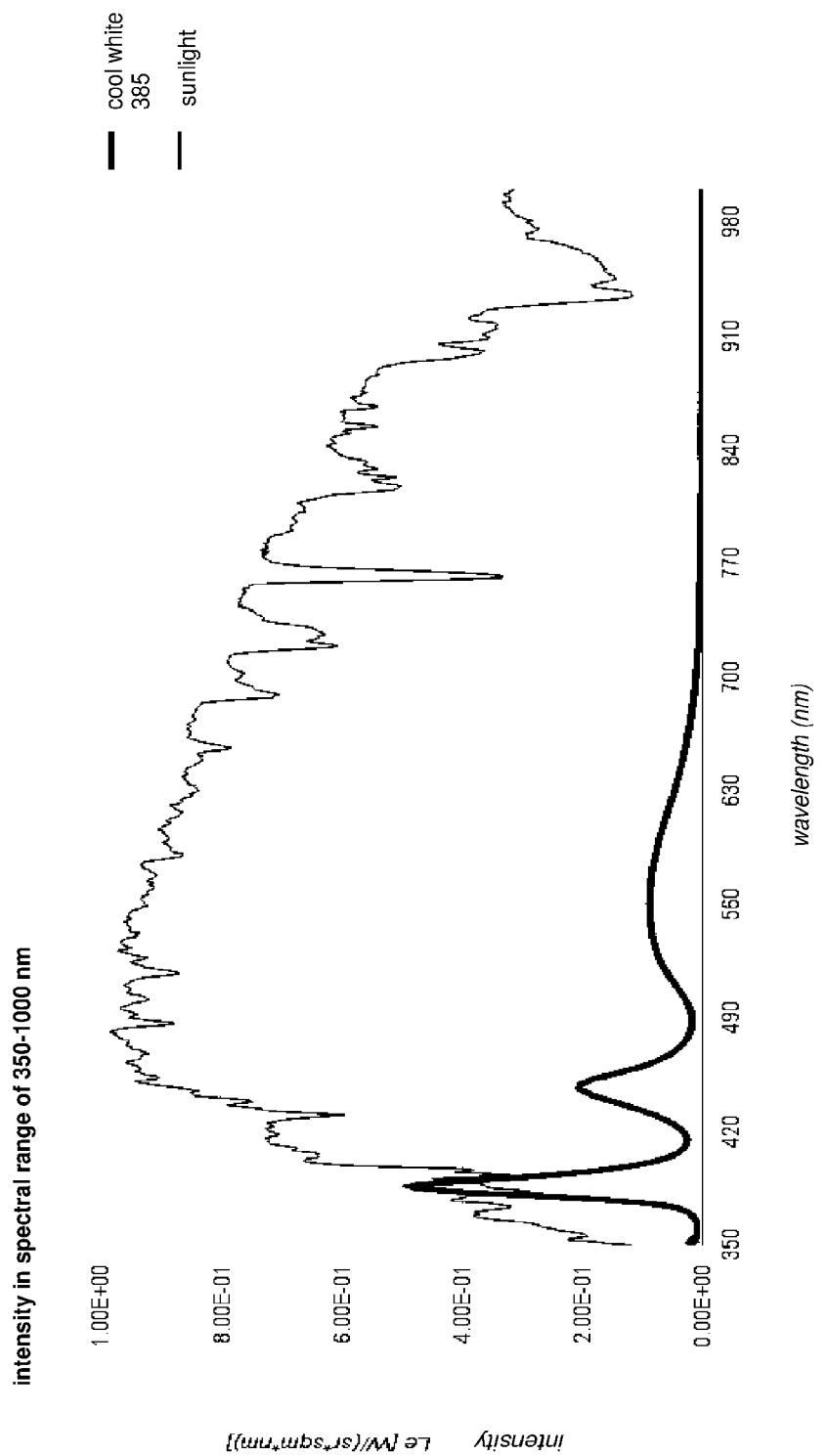
FIG. 3 shows the intensity in spectral range of 350-1000 nm. Combination 3: [cool white, 385 nm] compared to sunlight.

Example 1. Stimulation of *Hermetia illucens* Reproduction

A modular system with lamps emitting light in the near ultraviolet range having emission peaks of 375 nm, 385 nm 405 nm, 455 nm was used, allowing for control of lighting intensity, and for inclusion of individual spectral ranges. The system consisted of 8 LED lamps with a nominal power of 20 W, including 4 lamps emitting "cool white" light in the range of 400-800 nm and 4 lamps with a narrow spectral range having emission peaks at 375 nm, 385 nm 405 nm, 455 nm. The system enabled independent control of each lamp in the nominal range. The system was used in a plexiglass cabinet measuring 40×80×100 cm (W×L×H) with the bottom surface area of 0.32 m², equipped with a monitoring system monitoring temperature and air humidity providing an effective gravitational ventilation.

Three experiments on a group of insects of 100-130 subjects were performed. Subjects aged 2 days after transformation to the form of imago, ready for reproduction, were selected. Experiments were performed at temperature of 26° C. and a relative air humidity of 40%. Insects originated from the inventors breeding line.

In the experiments the mobility of insects (leaps to mating flight) was determined, 5 min after turning on the light of the given range and/or after exposure of insects to sunlight (sunny day, the sun at its zenith), expressed as a percentage of insects in flight in relation to the total number of insects and the number of insects connected during copulation 30 minutes after turning on the light of the given range or after exposure to sunlight, expressed as a percentage of insects during copulation in relation to the total number of insects. For each group between the individual measurements intervals of 60 minutes were retained. Each experiment used a different combination sequence of light sources.

Combinations of light sources utilized, including light intensity and irradiance are described in Table 1. Graphs of the spectrum for each combination compared to solar spectrum are shown in FIG. 1-5. Measurements were made with a calibrated device specbos 1211 UV from JETI Technische Instrumente GmbH. The results of experiments (n=3) are described in Table 2.

TABLE 1

Light intensity and irradiance in the utilized light sources combinations

|  | Light intensity (lx) | Irradiance (W/m²) 350-1000 nm |
|---|---|---|
| 1. 4 × cool white | 5165 | 19 |
| 2. 4 × cool white<br>1 × 375 nm<br>1 × 385 nm<br>1 × 405 nm<br>1 × 455 nm | 5590 | 43 |
| 3. 4 × cool white<br>1 × 385 nm | 5202 | 27 |
| 4. 4 × cool white<br>1 × 385 nm<br>1 × 405 nm | 5355 | 42 |
| 5. 4 × cool white<br>1 × 385 nm<br>1 × 405 nm<br>1 × 455 nm | 5522 | 42 |
| 6. sunlight | 67077 | 324 |

TABLE 2

Insect mobility and the percentage of copulating insects (n = 3) in the chamber, with the use of particular light combinations. Average values for triplicates.

|  | Percent of insects in flight [%] t = 5 | Percent of copulating insects [%] t = 30 |
|---|---|---|
| 1. 4 × cool white | 5.3 | 0 |
| 2. 4 × cool white<br>1 × 375 nm<br>1 × 385 nm<br>1 × 405 nm<br>1 × 455 nm | 77.6 | 52.3 |
| 3. 4 × cool white<br>1 × 385 nm | 58.2 | 40.2 |
| 4. 4 × cool white<br>1 × 385 nm<br>1 × 405 nm | 74.5 | 50.6 |
| 5. 4 × cool white<br>1 × 385 nm<br>1 × 405 nm<br>1 × 455 nm | 75.4 | 54.4 |
| 6. sunlight | 68.5 | 38.2 |

Example 2. Stimulation of Locusts Reproduction

The experiment was performed with the use of the system described in Example 1. The experiment was performed in temperature of 35° C. on groups of 50 adults (25.25.0), aged 7-12 days after the last moulting, of the species *Schistocerca gregaria* and *Locusta migratoria*. In the experiments the mobility and pairing of insects was assessed, 5 and 30 minutes after turning on the lights, respectively (Table 3).

TABLE 3

The percentage of paired insects (n = 1) in the chamber with the use of a particular light combination.

|  | Percentage of paired insects *Schostocerca gregaria* [%] | Percentage of paired insects *Locusta migratoria* [%] |
|---|---|---|
| 1. 4 × cool white | 20 | 16 |
| 2. 4 × cool white<br>1 × 375 nm<br>1 × 385 nm<br>1 × 405 nm<br>1 × 455 nm | 64 | 72 |
| 3. 4 × cool white<br>1 × 385 nm | 60 | 72 |
| 4. 4 × cool white<br>1 × 385 nm<br>1 × 405 nm | 64 | 68 |
| 5. 4 × cool white<br>1 × 385 nm<br>1 × 405 nm<br>1 × 455 nm | 68 | 76 |
| 6. sunlight | 68 | 76 |

CONCLUSIONS

Based on the research conducted with the use of the prototype lighting panel based on LED lamps, the Inventors confirmed the important role of light in the spectral range of 370-410 nm in reproductive behavior stimulation of *hermetia* and locusts.

White light in the range of 400-800 nm (Table 2 Item 1) does not stimulate *hermetia* to flight and mating activity. The inclusion of spectral lamps with a peak emission of 385 nm (Table 2 item 3) causes a rapid increase in activity, flies take flight and after 30 minutes they copulate intensively. Number of copulating insects is comparable to the number of copulating insects for the control (Table 2 item 6), i.e. sunlight measured on a sunny, cloudless day in the time of ascendancy of the sun at its zenith, which is an increase in the efficiency of reproduction in relation to the iodine-quartz lamp described in literature by approximately 50%.

This effect is intensified with the use of an additional light source with a peak emission of 405 nm (Table 2 item 4), which clearly indicates the important role of light in the range of 370-410 nm for the stimulation of *hermetia* reproductive behavior. It is significant that with the use of white light and two independent sources of light in the 370-410 nm band, having emission peaks of 385 nm and 405 nm with intensity exceeding the intensity of sunlight for these ranges (FIG. 2, 3, 4), the activity increase by approximately 25% compared to the results obtained for sunlight is observed. Simultaneously it has been shown that increasing intensity in additional spectral ranges of 375 nm and 455 nm (Table 2, item 2 and 5), did not significantly affect the activity of *hermetia*, suggesting that the use of additional lamps emitting light with peaks in this range may not be necessary.

Comparing the intensity of light and irradiance in the range above 410 nm (Table 1 item 1 and 5; FIG. 1) indicates that the total intensity of light and irradiance in the range of the visible spectrum, are of secondary importance for stimulating *hermetia* reproduction, and light emission limited to this range is not sufficient to stimulate reproduction (Table 2 item 1).

Figure 4:
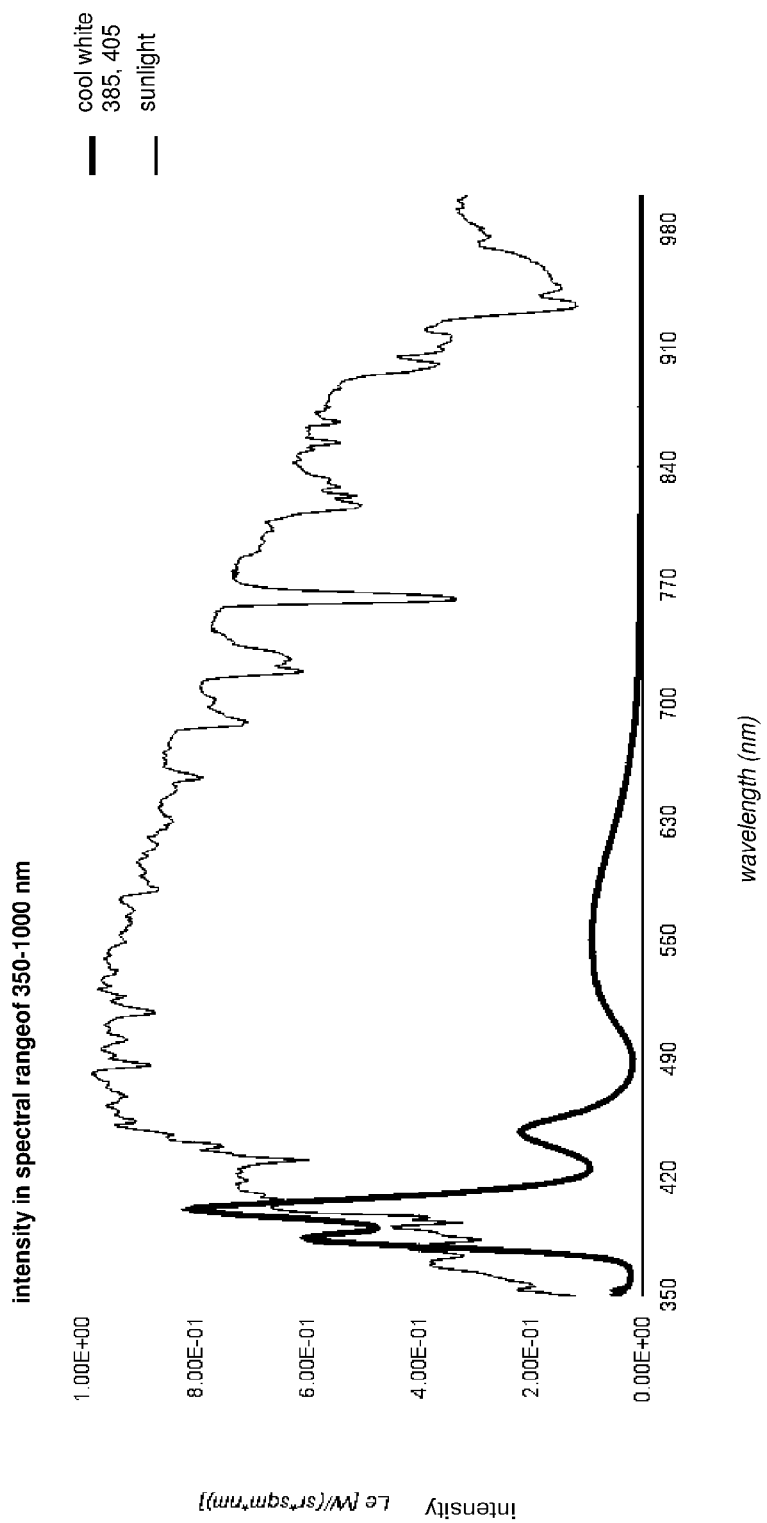
FIG. 4 shows the intensity in spectral range of 350-1000 nm. Combination 4: [Cool white, 385 nm, 405 nm] as compared with sunlight.
Figure 5:
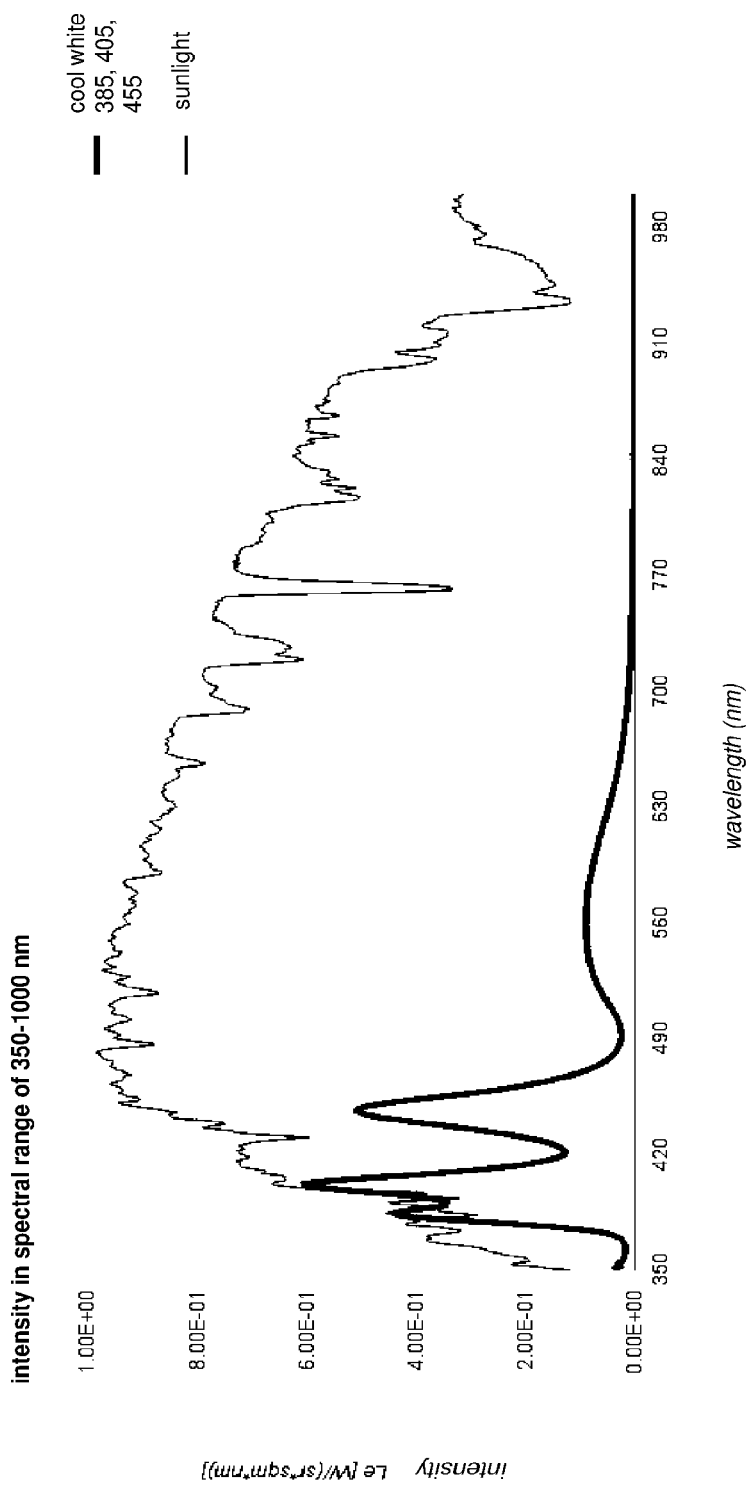
FIG. 5 shows the intensity in spectral range of 350-1000 nm. Combination 5: [cool white, 385 nm, 405 nm, 455 nm], compared with sunlight.

The 4$^{th}$ variant comprising 6 lamps with a total nominal power of 120 W was considered the best solution (Table 1 item. 4; FIG. 4). The solution according to the invention enables the reduction of energy consumption by about 70% compared to the energy consumption with the use of iodine-quartz lamps with the simultaneous improvement in reproduction efficiency.

The use of modular lamp system according to the invention enables to control the spectrum emission and the replacement of individual lamp modules without replacing the entire lighting system. Independent control of individual lamps can simulate light conditions of the natural environment, both in terms of light intensity and spectrum specific for latitudes of *hermetia*'s natural occurrence, as well as increasing irradiance spectrum below 455 nm above the levels found in the natural environment.

The use of the modular system according to the invention in closed breeding chambers for monitoring the state of insect population enables accurate and precise control of critical environmental parameters, while significantly reducing the space required for the reproduction, with respect to the solutions used in the industry, the present invention enabling efficient and effective stimulation of *hermetia* reproduction in a chamber with a height of 100 cm and having a bottom surface area not bigger than 0.32 m$^2$, thus several times smaller than the solutions described in literature (Tomberlin et al.; Zgang et al.).

Light in the range of 385-455 nm seems to play a key role in the stimulation of reproductive behavior of locust species *Locusta migratoria* and *Schistocerca gregaria*. Despite lower total irradiance in the range of 350-700 nm, the number of activate locust showing reproductive behavior was similar to the one with the use of natural light.

The invention claimed is:

1. A modular lamp system for breeding and stimulation of tropical insects reproduction which reproduction depends on intensity of sunlight which stimulates mobility of tropical insects and increase mating activity of the tropical insects selected from *Hermetia illucens, Locusta migratoria*, and *Schistocerca gregaria*, wherein said modular lamp system comprises:
   lamps emitting light in a range of 400-800 nm and at least one lamp with a peak emission in a range of 370-410 nm, wherein a light intensity of the modular lamp system measured at 50 cm from the lamps of the modular lamp system is no less than 5000 lx with irradiance in a spectral range of 350-1000 nm at a level of 35-50 W/m$^2$, wherein no less than 95% of the irradiance is in a range of 350-700 nm, and wherein irradiance in a spectral range of 370-410 nm is 25-80% of the irradiance in the range of 350-700 nm and is no less than 10 W/m$^2$, and
   wherein the light intensity in the range of 370-410 nm is higher than the intensity of sunlight in this range.

2. The modular lamp system according to claim 1, wherein all lamps included in the system are controlled independently.

3. The modular lamp system according to claim 1, wherein the lamps are LED lamps.

4. The modular lamp system according to claim 1, wherein at least one lamp has a peak emission of 385 nm.

5. The modular lamp system according to claim 4, further comprising a lamp having a peak emission of 405 nm.

6. The modular lamp system according to claim 5, comprising lamps of a total nominal power of about 120 W.

7. The modular lamp system according to claim 4, further comprising a lamp having a peak emission of 455 nm.

8. The modular lamp system according to claim 7, further comprising a lamp having a peak emission of 375 nm.

9. The modular lamp system according to claim 1, wherein the system is installed in a closed breeding chamber.

10. A method of insect breeding and reproduction stimulation in breeding chambers, comprising providing insects with a light source in a form of the modular lamp system according to claim 1.

11. The method of insect breeding and reproduction stimulation according to claim 10, wherein the insects are non-native to temperate climate zones.

12. The method of insect breeding and reproduction stimulation according to claim 10, wherein the insects are kept in a closed breeding chamber.

13. The modular lamp system according to claim 9, wherein the closed breeding chamber has a height lower than about 120 cm.

14. The modular lamp system according to claim 9, wherein the closed breeding chamber has a bottom surface area equal to or smaller than about 0.32 m$^2$.

15. The method according to claim 12, wherein the closed breeding chamber has a height lower than about 120 cm.

16. The method according to claim 12, wherein the closed breeding chamber has a bottom surface area equal to or smaller than about 0.32 m$^2$.

* * * * *